(12) United States Patent
Bernico et al.

(10) Patent No.: US 10,825,095 B1
(45) Date of Patent: Nov. 3, 2020

(54) USING IMAGES AND VOICE RECORDINGS TO FACILITATE UNDERWRITING LIFE INSURANCE

(71) Applicant: State Farm Mutual Automobile Insurance Company, Bloomington, IL (US)

(72) Inventors: Michael L. Bernico, Bloomington, IL (US); Jeffrey Myers, Normal, IL (US)

(73) Assignee: State Farm Mutual Automobile Insurance Company, Bloomington, IL (US)

( * ) Notice: Subject to any disclaimer, the term of this patent is extended or adjusted under 35 U.S.C. 154(b) by 917 days.

(21) Appl. No.: 15/266,033

(22) Filed: Sep. 15, 2016

Related U.S. Application Data

(60) Provisional application No. 62/242,127, filed on Oct. 15, 2015.

(51) Int. Cl.
*G06Q 40/08* (2012.01)
*G06T 7/00* (2017.01)

(52) U.S. Cl.
CPC .......... *G06Q 40/08* (2013.01); *G06T 7/0012* (2013.01); *G06T 2207/10004* (2013.01); *G06T 2207/30196* (2013.01)

(58) Field of Classification Search
CPC ........ G06Q 40/08; G06Q 40/02; G06Q 40/00; G06Q 40/025; G06Q 40/04; G06Q 40/06;
(Continued)

(56) References Cited

U.S. PATENT DOCUMENTS 8,355,933 B2 * 1/2013 Loy ................. G06Q 40/02
 705/35
8,447,637 B2 * 5/2013 Read .................. G06Q 40/08
 705/4
(Continued)

OTHER PUBLICATIONS

Orr Hirschauge;Title: Khosla Ventures Invests in Israeli Medical Imaging Startup Zebra; Wall Street Journal; (4 pages) http://blogs.wsj.com/digits/2015/04/06/khosla-ventures-invests-in-israeli-medical-imaging-startup-zebra/.
(Continued)

*Primary Examiner* — Edward Chang
*Assistant Examiner* — Slade E Smith
(74) *Attorney, Agent, or Firm* — Faegre Drinker Biddle & Reath

(57) ABSTRACT

A system and method for evaluating an insurance applicant as part of an underwriting process to determine one or more appropriate terms of life or other insurance coverage, such as premiums. A processing element employing a neural network is trained to correlate aspects of appearance and/or voice with personal and/or health-related characteristic. A database of images and/or voice recordings of individuals with known personal and/or health-related characteristics is provided for this purpose. The processing element is then provided with an image and/or voice recording of the insurance applicant. The image may be an otherwise non-diagnostic image, such as an ordinary "selfie." The trained processing element analyzes the image of the insurance applicant, with their permission or affirmative consent, to determine the personal and/or health-related characteristic for the insurance applicant, and then, based upon that analysis, facilitates the underwriting process and/or suggests the one or more appropriate terms of insurance coverage.

17 Claims, 4 Drawing Sheets

(58) Field of Classification Search
CPC ......... G06T 7/0012; G06T 2207/10004; G06T 2207/30196; G07C 5/008; G07C 5/08; G06F 19/328
USPC .......................................................... 705/4
See application file for complete search history.

(56) References Cited

U.S. PATENT DOCUMENTS

| | | | | |
|---|---|---|---|---|
| 8,705,875 | B1* | 4/2014 | Ricanek, Jr. | G06K 9/00288 382/159 |
| 9,235,813 | B1* | 1/2016 | Qian | G06K 9/6256 |
| 9,818,158 | B1* | 11/2017 | Devereaux | G06Q 40/025 |
| 10,043,217 | B1* | 8/2018 | Bolden | G06Q 40/08 |
| 10,156,848 | B1* | 12/2018 | Konrardy | G01C 21/34 |
| 2004/0153362 | A1* | 8/2004 | Bauer | G06Q 40/08 705/4 |
| 2005/0102172 | A1* | 5/2005 | Sirmans, Jr. | G06Q 40/08 705/4 |
| 2007/0118398 | A1* | 5/2007 | Perls | G16H 10/20 705/2 |
| 2009/0055227 | A1* | 2/2009 | Bakos | G06Q 40/08 705/4 |
| 2009/0119133 | A1* | 5/2009 | Yeransian | G06Q 40/08 705/4 |
| 2009/0210256 | A1* | 8/2009 | Upadhyayula | G06Q 40/08 705/4 |
| 2009/0240524 | A1* | 9/2009 | Bluth | G06F 19/3462 705/2 |
| 2010/0161357 | A1* | 6/2010 | Loy | G06Q 40/025 705/4 |
| 2010/0241465 | A1* | 9/2010 | Amigo | A61B 5/021 705/4 |
| 2011/0040582 | A1* | 2/2011 | Mullins | G06Q 40/08 705/4 |
| 2011/0161100 | A1* | 6/2011 | Peak | G06Q 50/22 705/2 |
| 2011/0213625 | A1* | 9/2011 | Joao | G06F 19/3418 705/3 |
| 2011/0213628 | A1* | 9/2011 | Peak | G06Q 40/08 705/4 |
| 2012/0123806 | A1* | 5/2012 | Schumann, Jr. | G06Q 40/08 705/4 |
| 2012/0330692 | A1* | 12/2012 | Read | G06Q 40/08 705/4 |
| 2013/0060582 | A1* | 3/2013 | Cutino | G06Q 40/08 705/4 |
| 2013/0090955 | A1* | 4/2013 | Gore | G06Q 40/08 705/4 |
| 2013/0223694 | A1* | 8/2013 | Ricanek, Jr. | G06T 11/206 382/118 |
| 2013/0290023 | A1* | 10/2013 | Hight | G16H 50/30 705/3 |
| 2014/0180980 | A1* | 6/2014 | Hido | G06N 20/00 706/12 |
| 2015/0025917 | A1* | 1/2015 | Stempora | G06K 9/0061 705/4 |
| 2015/0134344 | A1* | 5/2015 | Turrentine | G06F 19/328 705/2 |
| 2015/0235001 | A1* | 8/2015 | Fouts | G16H 10/60 705/2 |
| 2016/0125149 | A1* | 5/2016 | Abramowitz | G06F 19/328 705/3 |
| 2016/0259994 | A1* | 9/2016 | Ravindran | G06N 3/08 |

OTHER PUBLICATIONS

Dana Dovey; Title: Parkinson's Disease May One Day Be Identified With a Voice Analysis Smartphone App; Medical Daily; (6 pages); http://www.medicaldaily.com/parkinsons-disease-may-one-day-be-identified-voice-analysis-smartphone-app-278256.

Lina Zeldovich; Title: This app claims it can detect cancer by the sound of your voice; Digital Trends; (10 pages); http://www.digitaltrends.com/sports/kijini-health-app/.

(Fredo Durand, William T. Freeman, Guha Balakrisnan, Kathrine L. Bouman, Justin G. Chen, Abe Davis, Hossein Mobahi, Michael Rubinstein, Neal Wadhwa, Hao-Yu-Wu, and Tianfan Xue); Title: Video Magnification; (4 pages);http://people.csail.mil.edu/mrub/vidmag/.

Notice of Allowance for U.S. Appl. No. 15/266,118, filed Sep. 15, 2015; Inventor: Michael L. Bemico.

Selfie Quote—Using Microsoft's Oxford API to Provide Health Quotes, by Khalid Abuhakmeh; https://www.khalidabuhakmeh.com/selfie-quote-using-microsoft-s-oxford-api-to-provide-health-quotes.

* cited by examiner

USING IMAGES AND VOICE RECORDINGS TO FACILITATE UNDERWRITING LIFE INSURANCE

RELATED APPLICATIONS

The present patent application is a non-provisional patent application which claims priority benefit to U.S. Provisional Patent Application Ser. No. 62/242,127, entitled "USING IMAGES AND VOICE RECORDINGS TO FACILITATE UNDERWRITING LIFE INSURANCE", filed Oct. 15, 2015, which is hereby incorporated by reference in its entirety. Further, the present application is related to identically-titled co-pending U.S. Non-Provisional patent application Ser. No. 15/266,118, filed Sep. 15, 2016, which is also hereby incorporated by reference in its entirety.

FIELD OF THE INVENTION

The present disclosure generally relates to systems and methods for evaluating insurance applicants to facilitate underwriting insurance policies. More particularly, the present disclosure relates to a system and a computer-implemented method for analyzing still and/or moving (i.e., video) images, and/or voice recordings of insurance applicants as part of an underwriting process to determine appropriate insurance premiums and/or other terms of coverage.

BACKGROUND

The nature of the underwriting process for life insurance includes a number of factors which limit the ability to sell policies online. For example, some providers may require collecting samples of bodily fluids to assess an applicant's health status. Furthermore, even providers who do not require such samples are at risk of receiving fraudulent answers to personal and/or health-related questions, such as the applicant falsely claiming to be a non-smoker. Prior attempts to solve these problems include not selling high-benefit policies online, proxying the desired medical information with advanced statistical techniques using data from other sources, and pricing potential fraud into future policies.

Also, machine vision techniques have been employed to extract health-related information from images of people. For example, one machine vision platform is able to diagnose certain medical conditions based upon analyses of images from diagnostic imaging tools, such as an X-ray, a CT scan, and/or an MRI scan. The computer's diagnoses may even be able to identify certain conditions at earlier stages than doctors could identify them in some situations.

BRIEF SUMMARY

Embodiments of the present technology relate to systems and methods for analyzing still and/or moving (i.e., video) images and/or voice recordings of applicants as part of an underwriting process to determine appropriate life insurance premiums and/or other terms of coverage.

In a first aspect, a system for evaluating an insurance applicant as part of an underwriting process to determine one or more appropriate terms of insurance coverage may broadly comprise a communication element and a processing element. The communication element may be configured to receive an image of the insurance applicant. The processing element may be trained to probablistically correlate an aspect of appearance with a personal and/or health-related characteristic by being provided with a database of images of individuals having known personal and/or health-related characteristics. The trained processing element may be configured to analyze the image of the insurance applicant to probablistically determine the personal and/or health-related characteristic for the insurance applicant, and to suggest the appropriate term of insurance coverage based at least in part on the probablistically determined personal and/or health-related characteristic. The system may include more, fewer, or alternative components, including those discussed elsewhere herein.

In another aspect, a computer-implemented method for evaluating an insurance applicant as part of an underwriting process to determine one or more appropriate terms of insurance coverage may be provided. The method may include training a processing element to probablistically correlate an aspect of appearance with a personal and/or health-related characteristic by providing the processing element with a database of images of individuals having known personal or health-related characteristics. The method may include receiving with a communication element an image of the insurance applicant; analyzing the image of the insurance applicant with the trained processing element to probablistically determine the personal and/or health-related characteristic for the insurance applicant; and/or suggesting with the processing element the one or more appropriate terms of insurance coverage based at least in part on the probablistically determined personal and/or health-related characteristic. The computer-implemented method may include more, fewer, or alternative actions, including those discussed elsewhere herein.

In another aspect, a non-transitory computer-readable medium with an executable program stored thereon for evaluating an insurance applicant as part of an underwriting process to determine one or more appropriate terms of insurance coverage may broadly instruct a system (that includes a communication element and a processing element) to perform the following actions. The processing element may be trained to probablistically correlate an aspect of appearance with a personal and/or health-related characteristic by providing the processing element with a database of images of individuals having known personal or health-related characteristics. The communication element may be instructed to receive an image of the insurance applicant. The trained processing element may be instructed to analyze the image of the insurance applicant to probablistically determine the personal and/or health-related characteristic for the insurance applicant, and instructed to suggest the one or more appropriate terms of insurance coverage based at least in part on the probablistically determined personal and/or health-related characteristic. The non-transitory computer-readable medium with an executable program stored thereon may include more, fewer, or alternative instructions, including those discussed elsewhere herein.

Various implementations of any or all of the foregoing aspects may include any one or more of the following additional features. The insurance coverage may be life insurance coverage, and the one or more appropriate terms of insurance coverage may include an insurance premium. The image of the insurance applicant may be a digital, analog, still, or moving (i.e., video) image, and the image may be an otherwise non-diagnostic conventional image, such as a "selfie" taken by the insurance applicant. The processing element may be trained using supervised or unsupervised machine learning, and may employ a neural network, which may be a convolutional neural network or a deep learning neural network. The personal and/or health-related characteristic may be, for example, any one more of age, sex, weight, height, ethnicity, lifespan, cause of death, tobacco use, alcohol use, drug use, diet, and existing medical conditions, and/or risk factors for future medical conditions.

The communication element may be further configured to receive a voice recording of the insurance applicant. The processing element may be further trained to probablistically correlate an aspect of voice with the personal and/or health-related characteristic by being provided with a database of voice recordings of individuals having the known personal and/or health related characteristics. The processing element may be further configured to analyze the voice recording of the insurance applicant to probablistically determine the personal and/or health-related characteristic for the insurance applicant, and to suggest the appropriate term of insurance coverage based at least in part on the probablistically determined personal and/or health-related characteristic.

The processing element may be further configured to use the probablistically determined personal and/or health-related characteristic to verify information provided by the insurance applicant. The processing element may be further configured to use the probablistically determined personal and/or health-related characteristic to wholly or at least partially automatically determine the one or more appropriate terms of coverage.

Advantages of these and other embodiments will become more apparent to those skilled in the art from the following description of the exemplary embodiments which have been shown and described by way of illustration. As will be realized, the present embodiments described herein may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of systems and methods disclosed therein. It should be understood that each Figure depicts an embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals. The present embodiments are not limited to the precise arrangements and instrumentalities shown in the Figures.

Figure 1:
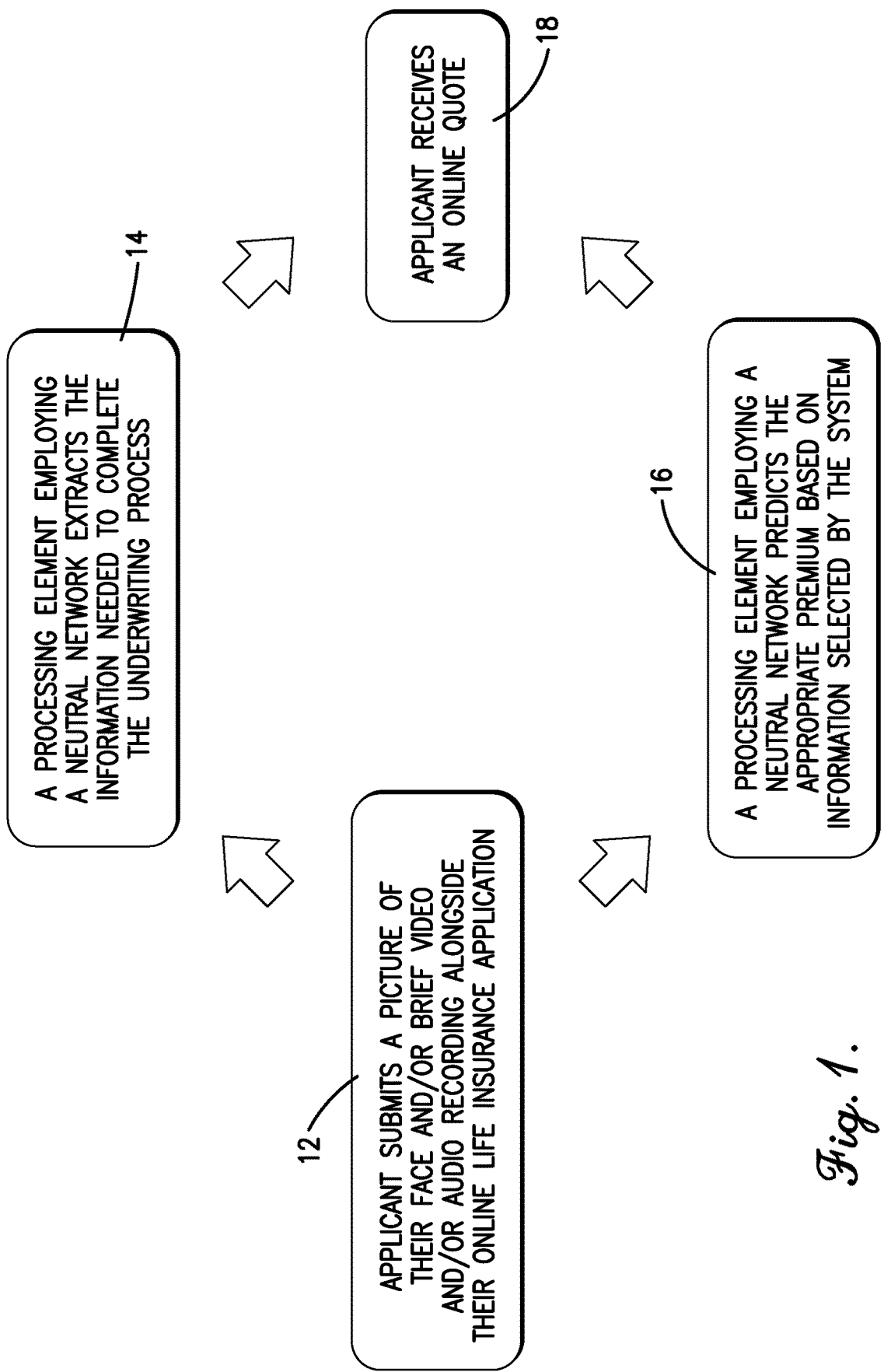
FIG. 1 is a high-level flowchart of an exemplary method embodiment of the present technology.

The Figures depict exemplary embodiments for purposes of illustration only. One skilled in the art will readily recognize from the following discussion that alternative embodiments of the systems and methods illustrated herein may be employed without departing from the principles of the invention described herein.

DETAILED DESCRIPTION

The present embodiments may relate to, inter alia, evaluating insurance applicants as part of an underwriting process to determine appropriate premiums and/or other terms of coverage. Broadly characterized, a processing element may be trained to probablistically analyze still and/or moving (i.e., video) images and/or voice recordings of applicants to determine personal and/or health-related information for an insurance provider. More specifically, an applicant desiring life or other insurance may provide such one or more still and/or moving (i.e., video) images and/or voice recordings of him- or herself to the insurance provider, and the processing element may analyze them to determine personal and/or health-related information relevant to an underwriting process. The information may be used to determine whether and under what terms, including appropriate premiums or discounts, the life or other insurance should be offered to the applicant.

Machine learning may involve identifying and recognizing patterns in existing data in order to facilitate making predictions for subsequent data. Models may be created based upon example inputs in order to make valid and reliable predictions for novel inputs. In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. In unsupervised machine learning, the processing element may be required to find its own structure in unlabeled example inputs. In one embodiment, machine learning techniques may be used to extract the relevant personal and/or health-related information for insurance applicants from images and/or voice recordings of those applicants without needing to acquire samples of bodily fluids or conduct conventional medical reviews.

In one embodiment, a processing element may be trained by providing it with a large sample of otherwise non-diagnostic conventional analog and/or digital, still and/or moving (i.e., video) images and/or voice recordings of persons with known personal and/or health-related information about the persons to analyze for correlations between detectable characteristics and the known information. Such information may include, for example, age, sex, weight, height, and ethnicity; tobacco, alcohol, and drug use; diet; existing medical conditions and risk factors for future medical conditions; lifespan and cause of death; and insurance premiums. Based upon these analyses, the processing element may learn how to identify characteristics and patterns that may then be applied to analyzing images of new insurance applicants. For example, the processing element may learn to determine the applicant's pulse from a video of the applicant, may learn to identify medication or other drug use by the applicant through, e.g., eye movement, and/or may learn to determine such other information as the applicant's glucose level. Similarly, the processing element may learn to identify indications of certain diseases, disorders, and/or behaviors from a voice recording of the applicant.

Referring to FIG. 1, once trained, the processing element may receive a still and/or moving (i.e., video) image and/or voice recording of an insurance applicant, and may probablistically determine the personal and/or health-related characteristic for the insurance applicant, as shown in 10. The resulting data may be used to complete the underwriting process, as shown in 12, such as verifying information provided by the applicant and/or answering underwriting questions, and/or may be used to substantially automate the underwriting process by directly predicting the appropriate insurance premium, as shown in 14. The applicant may then quickly be provided with a rate quote, as shown in 16.

The large sample of still and/or moving (e.g., video) images and/or voice recordings used to train the processing element may be, for example, provided by volunteers, existing policy holders, or taken from social media. The still and/or moving (e.g., video) image and/or voice recording received from the applicant may be analog or digital and otherwise non-diagnostic and conventional in nature, such as an ordinary "selfie" taken by the insurance applicant or him- or herself. The videos may include audio of the applicants' voices, and the processing element's training and analysis may include similarly seeking relevant characteristics or patterns in voices. The processing element's analyses of images may be probabilistic, such that the resulting data may be associated with varying degrees of certainty.

The processing element may employ a neural network, which may be a convolutional neural network (CNN) and/or a deep learning neural network. A CNN is a type of feed-forward neural network often used in facial recognition systems, in which individual neurons may be tiled so as to respond to overlapping regions in the visual field. A CNN may include multiple layers of small neuron collections which examine small portions of an input image, called receptive fields. The results of these collections may be tiled so that they overlap to better represent the original image, and this may be repeated for each layer. Deep learning involves algorithms that attempt to model high-level abstractions in data by using model architectures, with complex structures or otherwise, composed of multiple non-linear transformations. An image may be represented in various ways, such as a vector of intensity values per pixel, a set of edges, or regions of particular shape. Certain representations may better facilitate learning how to identify personal and health-related information from examples.

Thus, the present embodiments may be used to probablistically evaluate applicants for life or other insurance and determine appropriate premiums or other terms of coverage based upon analyses of still and/or moving images, and/or voice recordings of the applicants and without requiring conventional medical examinations.

Exemplary System

Figure 2:
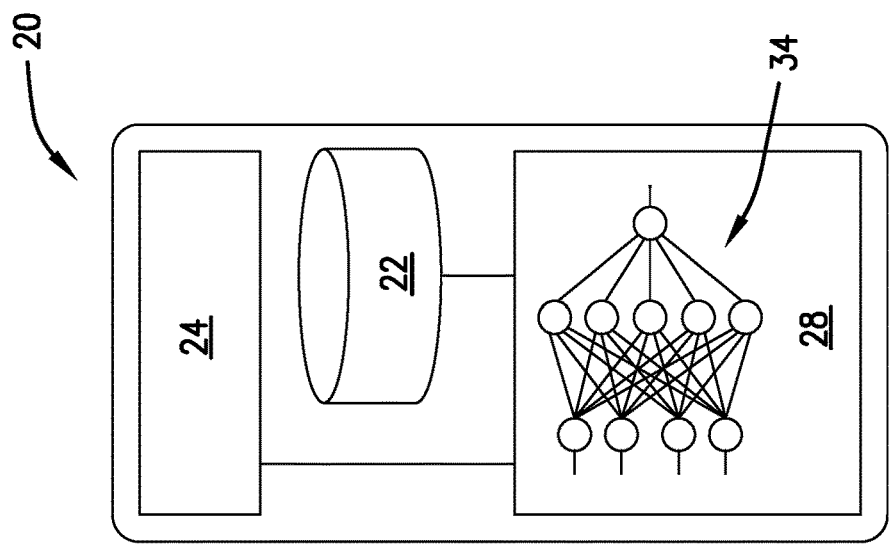
FIG. 2 is a diagram of an exemplary system constructed in accordance with embodiments of the present technology.
Figure 2:
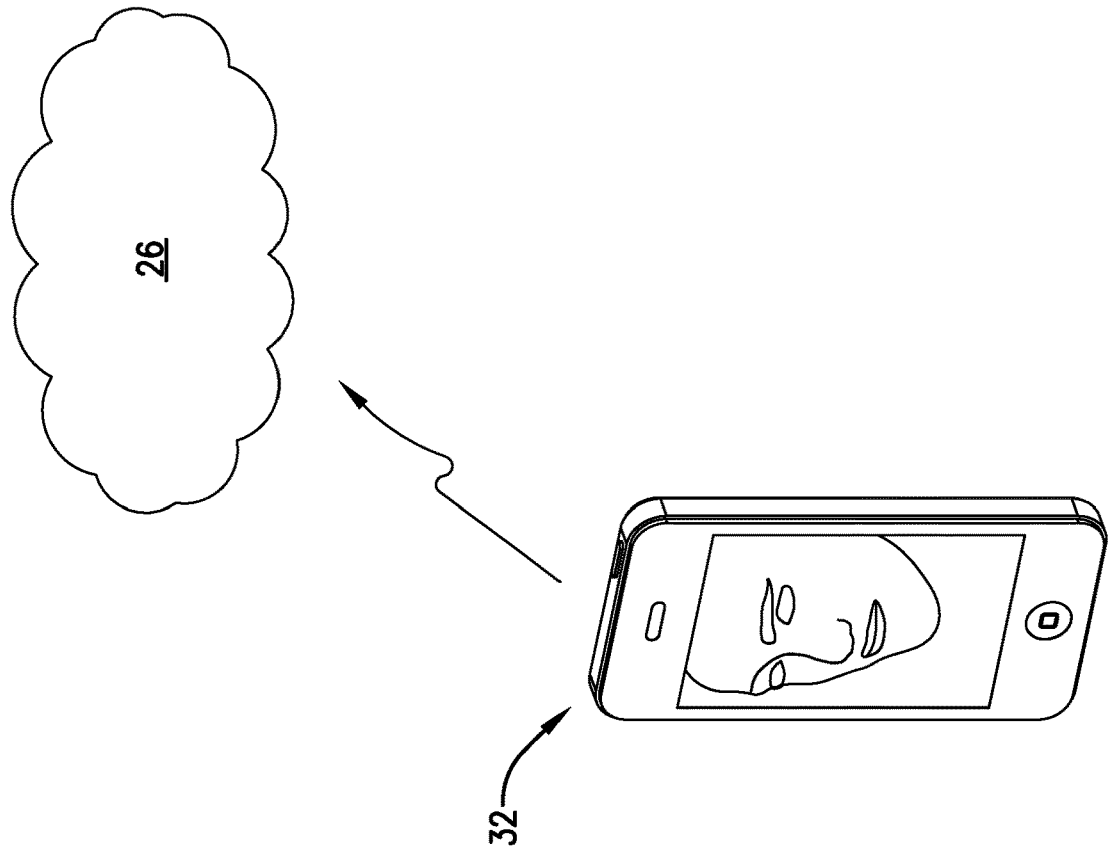

Referring to FIG. 2, an exemplary system 20 is shown configured for evaluating an insurance applicant as part of an underwriting process to determine one or more appropriate terms of life or other insurance coverage, which may include appropriate premiums. The system 20 may broadly comprise a memory element 22 configured to store information, such as the database of training images and/or voice recordings; a communication element 24 configured to receive and transmit signals via a network 26, including receiving the applicant's image and/or voice recording; and/or a processing element 28 trained and configured to analyze the applicant's image and/or voice recording.

More specifically, the memory element 22 may generally allow for storing information, such as the database of still and/or moving (e.g., video) images and/or voice recordings used to train the processing element 28, and still and/or moving (e.g., video) images and/or voice recordings received from applicants. The memory element 22 may include data storage components such as read-only memory (ROM), programmable ROM, erasable programmable ROM, random-access memory (RAM) such as static RAM (SRAM) or dynamic RAM (DRAM), cache memory, hard disks, floppy disks, optical disks, flash memory, thumb drives, USB ports, or the like, or combinations thereof. The memory element 22 may include, or may constitute, a "computer-readable medium." The memory element 22 may further store instructions, code, code segments, software, firmware, programs, applications, apps, services, daemons, or the like that are executed by the processing element 28. The memory element 22 may also store additional settings, data, documents, sound files, photographs, movies, images, databases, and the like. The memory element 22 may be electronically coupled or otherwise in electronic communication with the communication element 24 and the processing element 28.

The communication element 24 may generally allow for communication with remote systems or devices, including a system or device 32, such as a smartphone or other mobile communication device, configured to capture the still and/or moving (e.g., video) image and/or voice recording of the applicant. The communication element 24 may include signal or data transmitting and receiving circuits, such as antennas, amplifiers, filters, mixers, oscillators, digital signal processors (DSPs), and the like. The communication element 24 may establish communication wirelessly by utilizing radio-frequency (RF) signals and/or data that comply with communication standards such as cellular 2G, 3G, or 4G, IEEE 802.11 standard (such as WiFi), IEEE 802.16 standard (such as WiMAX), Bluetooth™, or combinations thereof. The communication element 24 may be electronically coupled or otherwise in electronic communication with the memory element 22 and the processing element 28.

The network 26 may be embodied by a local, metro, or wide area network (LAN, MAN, or WAN) and may be formed using a plurality of known architectures and topologies. In some embodiments, a portion of the network 26 may be formed by at least a portion of the Internet, by communication lines that are leased from other entities, or by combinations thereof. The network 26 may be implemented within a small area such as city or across a larger area such as a region or country.

The processing element 28 may be trained to probablistically correlate one or more aspects of appearance and/or voice with one or more personal or health-related characteristics by being provided with the database of still and/or moving (e.g., video) images and/or voice recordings stored in the memory element 22 of individuals having known personal or health-related characteristics. The processing element 28 may be configured to analyze the still and/or moving image and/or voice recording of the insurance applicant received via the communication element 24 to probablistically determine the personal or health-related characteristic for the insurance applicant to facilitate the completion of the underwriting process and/or to suggest one or more appropriate terms of insurance coverage, such as an appropriate premium, based at least in part on the probablistically determined personal or health-related characteristic. The processing element 28 may be trained using supervised or unsupervised machine learning. Further, the processing element 28 may employ a neural network 34, which may be a CNN or a deep learning neural network.

The processing element 28 may include one or more processors, microprocessors, microcontrollers, DSPs, field-programmable gate arrays (FPGAs), analog and/or digital application-specific integrated circuits (ASICs), or the like, or combinations thereof. The processing element 28 may generally execute, process, or run instructions, code, code segments, software, firmware, programs, applications, apps, processes, services, daemons, or the like. The processing element 28 may also include hardware components such as finite-state machines, sequential and combinational logic, and other electronic circuits that may perform the functions necessary for the operation of embodiments of the current inventive concept. The processing element 28 may be in electronic communication with the memory element 22 and the communication element 24. For example, the processing element 28 may communicate with these and possibly other electronic components through serial or parallel links that include address busses, data busses, control lines, and the like.

The system 20 may include more, fewer, or alternative components and/or perform more, fewer, or alternative actions, including those discussed elsewhere herein, and particularly those discussed in the following section describing the computer-implemented method.

Exemplary Computer-Implemented Method

Figure 3:
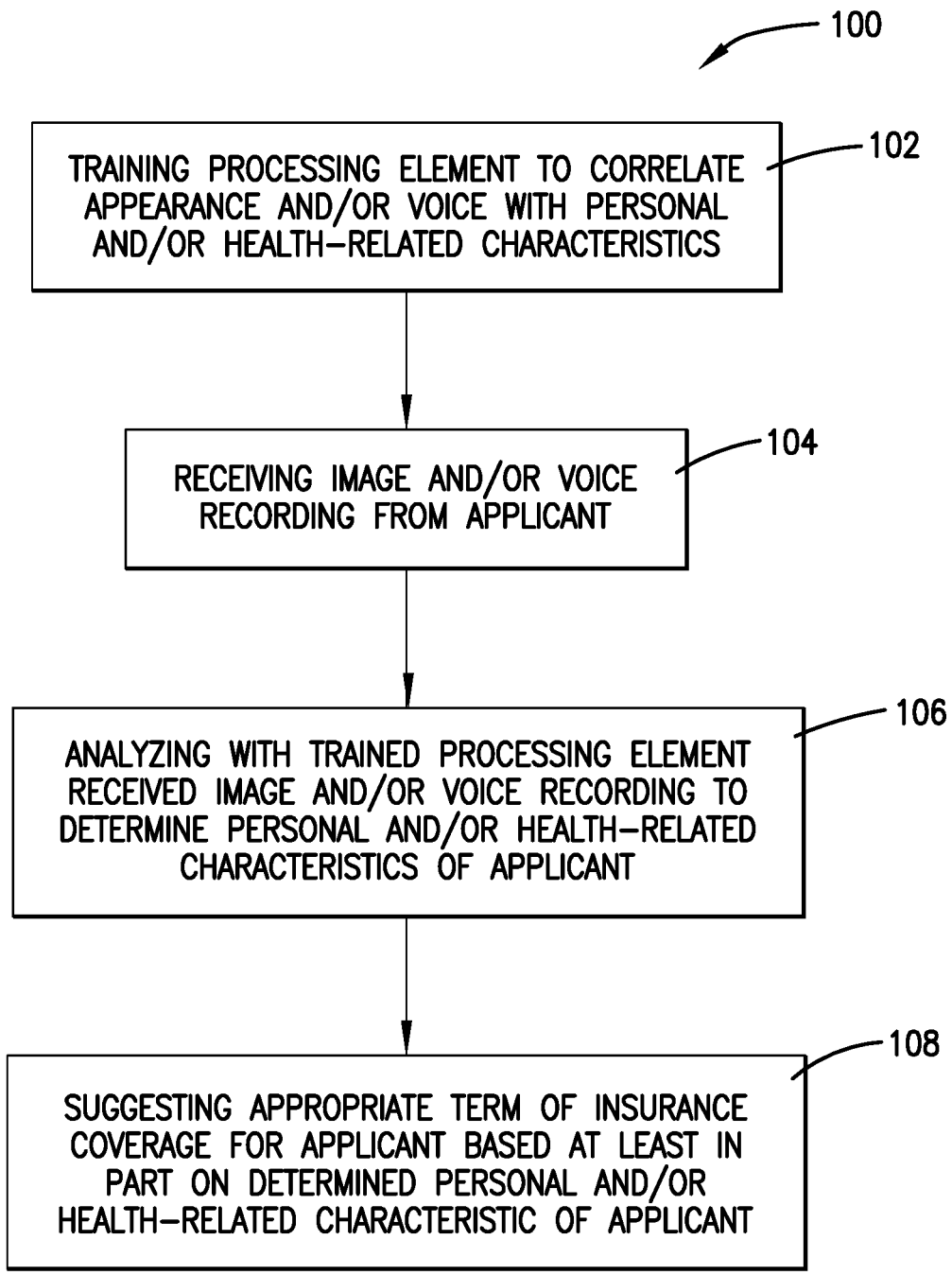
FIG. 3 is a flowchart of an exemplary computer-implemented method practiced in accordance with embodiments of the present technology.

Referring to FIG. 3, an exemplary computer-implemented method 100 is shown for evaluating an insurance applicant as part of an underwriting process to determine one or more appropriate terms of life or other insurance coverage, which may include appropriate premiums or discounts, such as discounts for risk averse individuals or those living a healthy life style. Broadly, the computer-implemented method may comprise the following actions. The processing element 28 may be trained to probablistically correlate a one or more aspects of appearance and/or voice with a personal or health-related characteristic by providing the processing element 28 with the database stored on the memory element 22 of still and/or moving (e.g., video) images and/or voice recordings of individuals having known personal or health-related characteristics, as shown in 102. The communication element 24 may receive the still and/or moving image and/or voice recording of the insurance applicant, as shown in 104. The still and/or moving (e.g., video) image and/or voice recording received from the applicant may be analog or digital and otherwise non-diagnostic and conventional in nature, such as an ordinary selfie taken by the insurance applicant or him- or herself. The trained processing element 28 may analyze the image of the insurance applicant to probablistically determine the personal or health-related characteristic for the insurance applicant, as shown in 106. The processing element 28 may suggest the appropriate term of insurance coverage, such as an appropriate premium, based at least in part on the probablistically determined personal or health-related characteristic, as shown in 108. The processing element 28 may be trained using supervised or unsupervised machine learning. Further, the processing element 28 may employ a neural network 34, which may be a CNN or a deep learning neural network.

The computer-implemented method may include more, fewer, or alternative actions, including those discussed elsewhere herein.

Exemplary Computer-Readable Medium

Referring again to FIGS. 2 and 3, an exemplary non-transitory computer-readable medium with one or more executable programs stored thereon may be configured for evaluating an insurance applicant as part of an underwriting process to determine one or more appropriate terms of life or other insurance coverage, which may include appropriate premiums. Broadly, the one or more programs may instruct the communication element 24, processing element 28, and/or other components of the system 20 to perform the following actions. The processing element 28 may be trained to probablistically correlate a one or more aspects of appearance and/or voice with a personal or health-related characteristic by providing the processing element 28 with the database stored on the memory element 22 of still and/or moving (e.g., video) images, and/or voice recordings of individuals having known personal or health-related characteristics, as shown in 102. The communication element 24 may be instructed to receive the still and/or moving image, and/or voice recording of the insurance applicant, as shown in 104. The still and/or moving image, and/or voice recording received from the applicant may be analog or digital and otherwise non-diagnostic and conventional in nature, such as an ordinary selfie taken by the insurance applicant or him- or herself. The trained processing element 28 may be instructed to analyze the image of the insurance applicant to probablistically determine the personal or health-related characteristic for the insurance applicant, as shown in 106. The processing element 28 may be instructed to suggest the appropriate term of insurance coverage, such as an appropriate premium, based at least in part on the probablistically determined personal and/or health-related characteristic, as shown in 108. The processing element 28 may be trained using supervised or unsupervised machine learning. Further, the processing element 28 may employ a neural network 34, which may be a CNN or a deep learning neural network.

The one or more executable programs stored on the non-transitory computer-readable medium may instruct the system 20 to perform more, fewer, or alternative actions, including those discussed elsewhere herein, and particularly those discussed in the section describing the computer-implemented method.

Exemplary Video Functionality

In one aspect, a video magnification system may use a short video of an applicant and extract the necessary health and personal data without the need for fluid samples or medical review. For example, the video may be used to calculate the applicant's pulse, and could evolve to detect medications or drug use through eye movements, and lead to other information such as glucose levels and other measurements normally attained through bodily fluid analysis. The results may be used to either answer underwriting questions or automate the underwriting process by predicting the appropriate premium directly. Also, the use of video magnification data may help prevent fraud by removing applicants' ability to enter fraudulent information and ensuring an applicant's identity.

In one embodiment, an online life or health insurance applicant may be filling out a virtual insurance application online, such as via their mobile device or another computing device. The virtual insurance application may ask the applicant to submit a short video or images of themselves, such as taken via their mobile device, for use with generating or adjusting an insurance quote, policy, premium, or discount (such as a life or health insurance application). The applicant may transmit the short video or images of themselves from their mobile device to an insurance provider remote server, or otherwise electronically attach the short video or images to the virtual insurance application. Then with the customer's permission or affirmative consent, the insurance provider remote server or another processor may analyze the short video or images, such as via video magnification or other digital image techniques, to identify risk, or lack thereof, associated with the applicant, or otherwise determine certain health characteristics of the applicant. For instance, pulse, heart rate, medication or drug use, cigarette or alcohol use, glucose levels, cholesterol level, age, weight, an amount of exercise, sex, etc. may be determined from video or image analysis (such as be noticing pulse movement or eye movement). As an example, cigarette use may be determined from image analysis of a person's teeth or gums, cholesterol level may be determined from image analysis of a person's eyes, pulse or heart rate may be determined from image analysis of a person's neck or veins.

Based upon the risk, or lack thereof identified, or health characteristics determined (such as pulse or glucose levels), the insurance provider may estimate an insurance premium or discount for the applicant, and transmit the insurance premium or discount to the applicant's mobile device, via wireless communication or data transmission, for the applicant's review, approval, or modification. As a result, an online customer shopping experience for life or health insurance may be enhanced, and the need for invasive procedures, such as giving blood, may be reduced.

Exemplary Audio Functionality

In another aspect, audio analysis techniques may use an audio recording of an applicant's voice and extract the necessary health and personal data without the need for fluid samples or medical review. The voice analysis system may learn to identify patterns and characteristics in voice recordings that are indicative of the presence of certain diseases or medications, or be able to detect other characteristics of an applicant, such as tobacco use. The results may be used to either answer underwriting questions or automate the underwriting process by predicting the appropriate premium directly. Further, the use of the audio analysis system may help prevent fraud by removing applicants' ability to enter fraudulent information and ensuring an applicant's identity.

In one embodiment, an online life or health insurance applicant may be filling out a virtual insurance application online, such as via their mobile device or another computing device. The virtual insurance application may ask the applicant to submit a short audio of themselves, such as recorded via their mobile device (e.g., voice recorded within a video), for use with generating or adjusting an insurance quote, policy, premium, or discount (such as a life or health insurance application). The applicant may transmit the short audio recording of themselves from their mobile device to an insurance provider remote server, or otherwise electronically attach the short audio recording to the virtual insurance application. Then with the customer's permission or affirmative consent, the insurance provider remote server or another processor may analyze the short audio recording, such as via audio analysis or other digital audio processing techniques, to identify risk, or lack thereof, associated with the applicant, or otherwise determine certain health characteristics of the applicant. For instance, certain diseases or medication use, as well as cigarette use, age, weight, sex may be determined or estimated from audio analysis. Based upon the risk, or lack thereof identified, or health characteristics determined (such as lack of smoking), the insurance provider may estimate an insurance premium or discount for the applicant, and transmit the insurance premium or discount to the applicant's mobile device, via wireless communication or data transmission, for the applicant's review, approval, or modification.

Exemplary Computer-Implemented Methods

Figure 4:
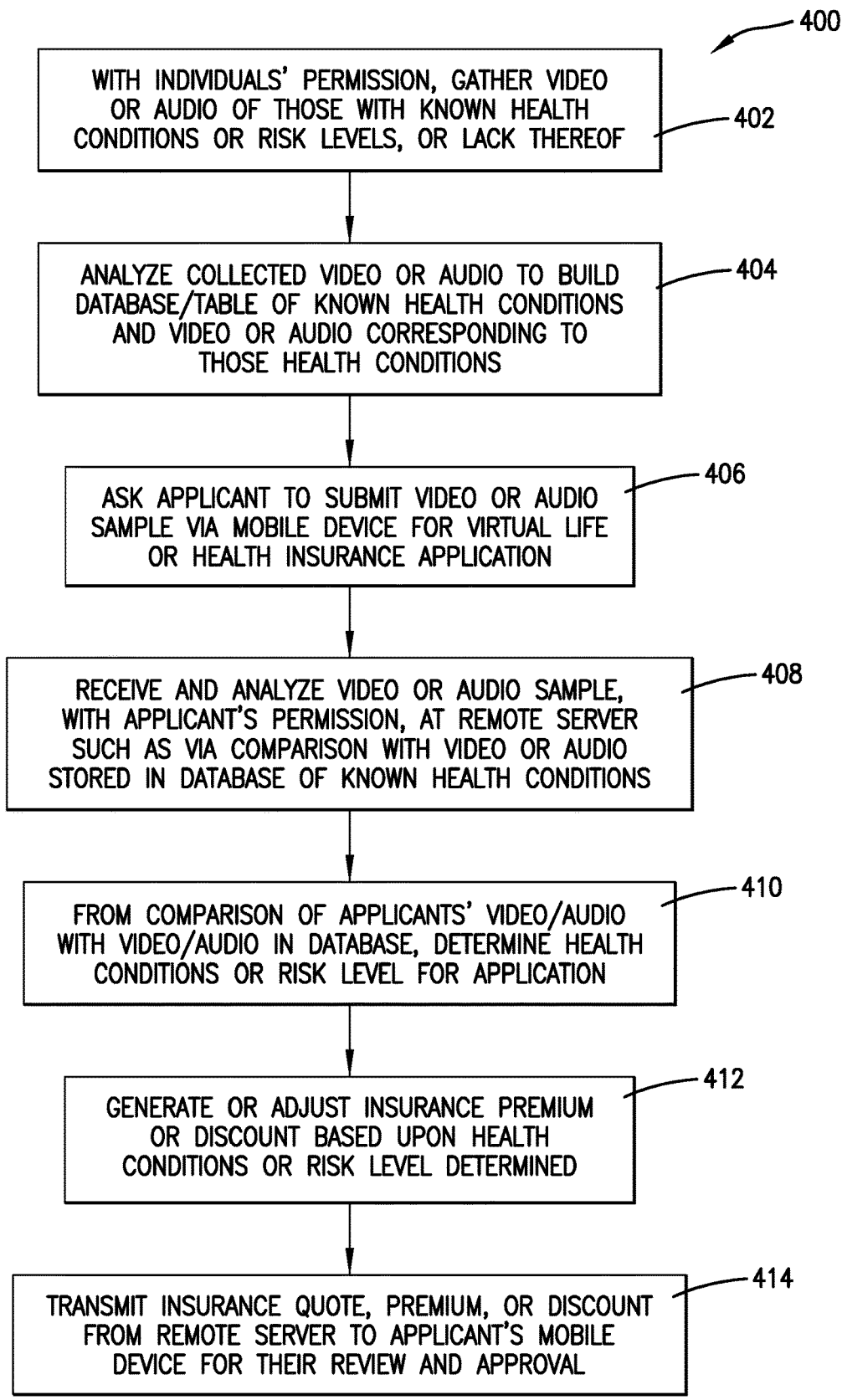
FIG. 4 depicts an exemplary computer-implemented method of providing life or health insurance quotes based upon, at least in part, video, image, or audio data samples received via wireless communication or data transmission from an applicant's mobile device.

FIG. 4 depicts an exemplary computer-implemented method 400 of providing life or health insurance quotes based upon, at least in part, video, image, or audio data samples received via wireless communication or data transmission from an applicant's mobile device. The method 400 may include with an individuals' permission, gathering video, images, or audio of those with known health conditions or risk levels, or lack thereof 402. For instance, images, images, and/or audio of those with certain diseases, associated with certain medication or drug use, associated with cigarette or alcohol usage, of a certain age or weight, of a specific cholesterol or glucose level, or having other specific health conditions or risk levels, or a lack of a health condition or ailment, or having a low risk level.

The method 400 may include analyzing the collected video, image(s), or audio to build a database, table or other data structure corresponding to the known health conditions 404. For instance, a two column data structure could include exemplary video, image(s), or audio (stored or linked to by a pointer in column 1) that is associated with a certain health condition or risk level (that is stored in column 2 of the data structure or table). Additionally or alternatively, instead of building a database, a neural network may be trained to identify certain health conditions or risk levels from processor analysis of video, images, or audio of individuals having known health conditions or ailments, such as described elsewhere herein.

The method 400 may include asking an insurance applicant to submit a video, image, or audio sample via their mobile device for a virtual life or health insurance application 406. For instance, after a database or neural network is trained to identify health conditions or health risk from video, image, or audio analysis, an online or virtual insurance application form may include functionality that allows an application to attach a video, image, or audio sample to a virtual application using their mobile device. The virtual application may give an applicant the option submitting video, image, or audio data of themselves, and ask for consent for an insurance provider to analyze the data sample submitted. In return, the applicant may not be required to submit to invasive procedures, such as drawing blood (or even a visit to nurse or doctor), and risk averse applicants may be entitled to a discount, such as those that don't smoke or drink heavily, or that exercise or otherwise live a health conscious life.

The method 400 may include analyzing the video, image, or audio data sample received from the application with the applicant's permission or affirmative consent 408. For instance, the applicant's mobile device may transmit the video, image, or audio data sample to an insurance provider remote server, and the data sample may be analyzed via comparison of video, image, or audio data stored in the database of known health conditions, or otherwise used to train a neural network.

The method 400 may include, from comparison of the online applicants' video, image, or audio data sample with video, image, audio data stored in the database (or used to train the neural network) to determine health conditions or risk level for the applicant 410. From analysis of the data sample various health conditions may be determined via a processor, such sex, weight, body mass index, cholesterol, amount of exercise, cigarette or alcohol use, medication or drug use, certain diseases or ailments, glucose levels, and other health conditions or risks, including those discussed elsewhere herein.

The method 400 may include generating or adjusting (such as at an insurance provider remote server) an insurance policy, premium, or discount based upon the health conditions or risk levels determined 412. For instance, risk averse applicants may have their lack of risk verified via their video, image, or data samples, such as lack of smoking or drug use, or an appropriate amount of exercise. As a result, those applicants may be receive an online insurance discount on health or life insurance, for instance.

The method 400 may include transmitting an insurance quote, premium, or discount from an insurance provider remote server to the applicant's mobile device for their review and approval 414. For instance, a quote for insurance may be transmitted to an applicant's mobile or other computing device for their review and approval via wireless communication and/or data transmission to enhance on online customer experience associated with shopping for and/or receiving binding life or health insurance.

In another aspect, a computer-implemented method for evaluating an insurance applicant as part of an underwriting process to determine a life or health insurance policy, premium, or discount may be provided. The computer-implemented method may include (1) training a processing element to probablistically correlate an aspect of appearance with a personal and/or health-related characteristic by providing the processing element with a database of images of individuals having known personal or health-related characteristics; (2) receiving with a communication element an image of the insurance applicant; (3) analyzing the image of the insurance applicant with the trained processing element to probablistically determine the personal and/or health-related characteristic for the insurance applicant; and/or (4) generating or adjusting via the processing element a life or health insurance policy, premium, or discount based at least in part on the probablistically determined personal and/or health-related characteristic.

The personal and/or health-related characteristic may be a pulse or heart rate. The personal and/or health-related characteristic may indicate, or be associated with, smoking, a lack of smoking, or an amount or frequency of smoking. The personal and/or health-related characteristic may indicate, or be associated with, drug or alcohol use, a lack of drug or alcohol use, or an amount or frequency of drug or alcohol use.

In another aspect, a computer-implemented method for evaluating an insurance applicant as part of an underwriting process to determine an appropriate life insurance premium may be provided. The computer-implemented method may include (1) training a processing element having a neural network to probablistically correlate one or more aspects of appearance with a personal and/or health-related characteristic by providing the processing element with a database of otherwise non-diagnostic conventional images of individuals having known personal and/or health-related characteristics; (2) receiving with a communication element an otherwise non-diagnostic conventional image of the insurance applicant; (3) analyzing with the trained processing element the otherwise non-diagnostic conventional image of the insurance applicant to probablistically determine the personal and/or health-related characteristic for the insurance applicant; (4) using, by the processing element, the probablistically determined personal and/or health-related characteristic to verify information provided by the insurance applicant; and/or (5) automatically determining or adjusting with the processing element a life or health insurance premium or discount based at least in part on the probablistically determined personal and/or health-related characteristic.

In another aspect, a computer-implemented method for evaluating applicant provided images to adjust or generate a life or health insurance policy, premium, or discount may be provided. The computer-implemented method may include (1) receiving, via one or more processors, image data from an applicant's mobile device; (2) comparing, via the one or more processors, the image data with images stored in a database that have corresponding pre-determined health conditions or risk levels; (3) identifying, via the one or more processors, a health condition or risk level for the applicant based upon the comparison of the applicant's image data with the images stored in the database; and/or (4) automatically determining or adjusting, via the one or more processors, a life or health insurance premium or discount based at least in part on the health condition or risk level for the applicant that is determined from their image data to facilitate providing more accurate or appropriate insurance premiums in view of risk, or lack thereof, to insurance customers. The health condition or risk level may be associated with or determined based upon whether or not the applicant smokes, or an amount that the applicant smokes (determined from processor analysis of the applicant's image data). The health condition or risk level may be associated with, or determined based upon, whether or not the applicant uses drugs, or pulse or heart rate of the applicant determined from processor analysis of the applicant's image data.

In another aspect, a computer-implemented method for evaluating applicant provided images to adjust or generate a life or health insurance policy, premium, or discount may be provided. The computer-implemented method may include (1) receiving, via one or more processors (and/or associated transceivers, such as via wireless communication or data transmission), an indication from an applicant's mobile device that the applicant is interested in applying for insurance and/or receiving an online insurance application from the applicant's mobile device; (2) transmitting, via the one or more processors (and/or associated transceivers), a request for the applicant to transmit image data of the applicant from their mobile device for use with determining an accurate insurance premium or discount; (3) receiving, via one or more processors (and/or associated transceivers), the image data from the applicant's mobile device; (4) identifying, via the one or more processors, a health condition or risk level for the applicant (and/or a personal and/or health-related characteristic) based upon the computer analysis of the applicant's image data; (5) automatically determining or adjusting, via the one or more processors, a life or health insurance premium or discount based at least in part on the health condition or risk level for the applicant that is determined from their image data; and/or (6) transmitting, via the one or more processors (and/or an associated transceiver), the life or health insurance premium or discount to the applicant's mobile device for their review and/or approval to facilitate providing more accurate insurance premiums to insurance customers and enhancing the online customer experience. The health condition or risk level (and/or personal and/or health-related characteristic) determined from computer analysis of the applicant's image data may be a pulse or heart rate. The health condition or risk level (and/or personal and/or health-related characteristic) determined from computer analysis of the applicant's image data may indicate, or may be associated with, smoking, a lack of smoking, or an amount or frequency of smoking. Additionally or alternatively, the health condition or risk level (and/or personal and/or health-related characteristic) determined from computer analysis of the applicant's image data may indicate, or be associated with, drug or alcohol use, a lack of drug or alcohol use, or an amount or frequency of drug or alcohol use.

In another aspect, a computer-implemented method for evaluating applicant provided audio to adjust or generate a life or health insurance policy, premium, or discount may be provided. The computer-implemented method may include (1) receiving, via one or more processors, an indication from an applicant's mobile device that the applicant is interested in applying for insurance and/or receiving an online insurance application from the applicant's mobile device; (2)

transmitting, via the one or more processors, a request for the applicant to transmit audio data of the applicant from their mobile device for use with determining an accurate insurance premium or discount; (3) receiving, via one or more processors, the audio data from the applicant's mobile device; (4) identifying, via the one or more processors, a health condition or risk level for the applicant (and/or a personal and/or health-related characteristic) based upon the computer analysis of the applicant's audio data; (5) automatically determining or adjusting, via the one or more processors, a life or health insurance premium or discount based at least in part on the health condition or risk level for the applicant that is determined from their audio data; and/or (6) transmitting, via the one or more processors, the life or health insurance premium or discount to the applicant's mobile device for their review and/or approval to facilitate providing more accurate insurance premiums to insurance customers and enhancing the online customer experience.

The foregoing methods may include additional, less, or alternate functionality, including that discussed elsewhere herein. Further, the foregoing methods may be implemented via one or more local or remote processors and/or transceivers, and/or via computer-executable instructions stored on non-transitory computer-readable medium or media.

Exemplary Computer Systems

In one aspect, a computer system for evaluating an insurance applicant as part of an underwriting process to determine one or more appropriate terms of insurance coverage may be provided. The system may include a communication element configured to receive an image of the insurance applicant; and a processing element—trained to probablistically correlate an aspect of appearance with a personal and/or health-related characteristic by being provided with a database of images of individuals having known personal and/or health-related characteristics, and configured to analyze the image of the insurance applicant to probablistically determine the personal and/or health-related characteristic for the insurance applicant, and to generate a proposed life or health insurance policy, premium, or discount for the insurance applicant based upon the personal and/or health-related characteristic probablistically determined from the image.

The communication element may be further configured to receive an voice recording of the insurance applicant; and the processing element is—trained to probablistically correlate an aspect of voice with the personal and/or health-related characteristic by being provided with a database of voice recordings of individuals having the known personal and/or health related characteristics, and configured to analyze the voice recording of the insurance applicant to probablistically determine the personal and/or health-related characteristic for the insurance applicant, and generate or adjust a proposed life or health insurance policy, premium, or discount based upon at least in part the probablistically determined personal and/or health-related characteristic.

The personal and/or health-related characteristic may be a pulse or heart rate. The personal and/or health-related characteristic may indicate, or be associated with, smoking, a lack of smoking, or an amount or frequency of smoking. The personal and/or health-related characteristic may indicate, or be associated with, alcohol or drug use, a lack of alcohol or drug use, or an amount or frequency of alcohol or drug use.

In another aspect, a computer system for evaluating an insurance applicant as part of an underwriting process to determine a life or health insurance policy, premium, or discount may be provided. The computer system may include one or more processors configured to: (1) train a processing element to probablistically correlate an aspect of appearance with a personal and/or health-related characteristic by providing the processing element with a database of images of individuals having known personal or health-related characteristics; (2) receive with a communication element an image of the insurance applicant; (3) analyze the image of the insurance applicant with the trained processing element to probablistically determine the personal and/or health-related characteristic for the insurance applicant; and/or (4) generate or adjust via the processing element a life or health insurance policy, premium, or discount based at least in part on the probablistically determined personal and/or health-related characteristic.

In another aspect, a computer system for evaluating an insurance applicant as part of an underwriting process to determine an appropriate life insurance premium may be provided. The computer system may include one or more processors configured to: (1) train a processing element having a neural network to probablistically correlate one or more aspects of appearance with a personal and/or health-related characteristic by providing the processing element with a database of otherwise non-diagnostic conventional images of individuals having known personal and/or health-related characteristics; (2) receive with a communication element an otherwise non-diagnostic conventional image of the insurance applicant; (3) analyze with the trained processing element the otherwise non-diagnostic conventional image of the insurance applicant to probablistically determine the personal and/or health-related characteristic for the insurance applicant; (4) use, by or via the processing element, the probablistically determined personal and/or health-related characteristic to verify information provided by the insurance applicant; and/or (5) automatically determine or adjust with the processing element a life or health insurance premium or discount based at least in part on the probablistically determined personal and/or health-related characteristic.

In another aspect, a computer system for evaluating applicant provided images to adjust or generate a life or health insurance policy, premium, or discount may be provided. The computer system may include one or more processors and/or associated transceivers configured to: (1) receive image data from an applicant's mobile device, such as via wireless communication or data transmission; (2) compare the image data with images stored in a database that have corresponding pre-determined health conditions or risk levels; (3) identify a health condition or risk level (such as low, medium, or high risk) for the applicant based upon the comparison of the applicant's image data with the images stored in the database; and/or (4) automatically determine or adjust a life or health insurance premium or discount based at least in part on the health condition or risk level for the applicant that is determined from their image data to facilitate providing more accurate or appropriate insurance premiums in view of risk, or lack thereof, to insurance customers. The health condition or risk level may be associated with or determined based upon whether or not the applicant smokes, or an amount that the applicant smokes (determined from processor analysis of the applicant's image data). The health condition or risk level may be associated with, or determined based upon, whether or not the applicant uses drugs, or pulse or heart rate of the applicant determined from processor analysis of the applicant's image data.

In another aspect, a computer system for evaluating applicant provided images to adjust or generate a life or health insurance policy, premium, or discount may be provided. The computer system may include one or more processors and/or transceivers configured to: (1) receive an indication, via wireless communication or data transmission, from an applicant's mobile device that the applicant is interested in applying for insurance and/or receive an online or virtual insurance application from the applicant's mobile device; (2) transmit, via wireless communication or data transmission, a request for the applicant to transmit image data of the applicant from their mobile device for use with determining an accurate insurance premium or discount; (3) receive, via wireless communication or data transmission, the image data from the applicant's mobile device; (4) identify or determine a health condition or risk level for the applicant (and/or a personal and/or health-related characteristic) based upon the computer analysis of the applicant's image data (with the customer's permission or affirmative consent); (5) automatically determine or adjust a life or health insurance premium or discount based at least in part on the health condition or risk level for the applicant that is determined from their image data; and/or (6) transmit an estimated insurance premium or discount to the applicant's mobile device for their review and approval to facilitate providing more accurate insurance premiums to insurance customers and enhancing the online customer experience.

In another aspect, a computer system configured for evaluating applicant provided audio to adjust or generate a life or health insurance policy, premium, or discount may be provided. The computer system may include one or more processors and/or transceivers configured to: (1) receive an indication from an applicant's mobile device that the applicant is interested in applying for insurance and/or receiving an online insurance application from the applicant's mobile device; (2) transmit a request for the applicant to transmit audio data of the applicant from their mobile device for use with determining an accurate insurance premium or discount; (3) receive the audio data from the applicant's mobile device; (4) identify or determine a health condition or risk level for the applicant (and/or a personal and/or health-related characteristic) based upon the computer analysis of the applicant's audio data (with the customer's permission or affirmative consent); (5) automatically determine or adjust a life or health insurance premium or discount based at least in part on the health condition or risk level for the applicant that is determined from their audio data; and/or (6) transmit the life or health insurance premium or discount to the applicant's mobile device for their review and/or approval to facilitate providing more accurate insurance premiums to insurance customers and enhancing the online customer experience.

The foregoing computer systems may be configured with additional, less, or alternate functionality, including that discussed elsewhere herein and that described with respect to FIG. 4. The foregoing computer systems may include computer-executable instructions stored on non-transitory computer-readable medium or media.

Additional Considerations

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology may include a variety of combinations and/or integrations of the embodiments described herein.

Although the present application sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as computer hardware that operates to perform certain operations as described herein.

In various embodiments, computer hardware, such as a processing element, may be implemented as special purpose or as general purpose. For example, the processing element may comprise dedicated circuitry or logic that is permanently configured, such as an application-specific integrated circuit (ASIC), or indefinitely configured, such as an FPGA, to perform certain operations. The processing element may also comprise programmable logic or circuitry (e.g., as encompassed within a general-purpose processor or other programmable processor) that is temporarily configured by software to perform certain operations. It will be appreciated that the decision to implement the processing element as special purpose, in dedicated and permanently configured circuitry, or as general purpose (e.g., configured by software) may be driven by cost and time considerations.

Accordingly, the term "processing element" or equivalents should be understood to encompass a tangible entity, be that an entity that is physically constructed, permanently configured (e.g., hardwired), or temporarily configured (e.g., programmed) to operate in a certain manner or to perform certain operations described herein. Considering embodiments in which the processing element is temporarily configured (e.g., programmed), each of the processing elements need not be configured or instantiated at any one instance in time. For example, where the processing element comprises a general-purpose processor configured using software, the general-purpose processor may be configured as respective different processing elements at different times. Software may accordingly configure the processing element to constitute a particular hardware configuration at one instance of time and to constitute a different hardware configuration at a different instance of time.

Computer hardware components, such as communication elements, memory elements, processing elements, and the like, may provide information to, and receive information from, other computer hardware components. Accordingly, the described computer hardware components may be regarded as being communicatively coupled. Where multiple of such computer hardware components exist contemporaneously, communications may be achieved through signal transmission (e.g., over appropriate circuits and buses) that connect the computer hardware components. In embodiments in which multiple computer hardware components are configured or instantiated at different times, communications between such computer hardware components may be achieved, for example, through the storage and retrieval of information in memory structures to which the multiple computer hardware components have access. For example, one computer hardware component may perform an operation and store the output of that operation in a memory device to which it is communicatively coupled. A further computer hardware component may then, at a later time, access the memory device to retrieve and process the stored output. Computer hardware components may also initiate communications with input or output devices, and may operate on a resource (e.g., a collection of information).

The various operations of example methods described herein may be performed, at least partially, by one or more processing elements that are temporarily configured (e.g., by software) or permanently configured to perform the relevant operations. Whether temporarily or permanently configured, such processing elements may constitute processing element-implemented modules that operate to perform one or more operations or functions. The modules referred to herein may, in some example embodiments, comprise processing element-implemented modules.

Similarly, the methods or routines described herein may be at least partially processing element-implemented. For example, at least some of the operations of a method may be performed by one or more processing elements or processing element-implemented hardware modules. The performance of certain of the operations may be distributed among the one or more processing elements, not only residing within a single machine, but deployed across a number of machines. In some example embodiments, the processing elements may be located in a single location (e.g., within a home environment, an office environment or as a server farm), while in other embodiments the processing elements may be distributed across a number of locations.

Unless specifically stated otherwise, discussions herein using words such as "processing," "computing," "calculating," "determining," "presenting," "displaying," or the like may refer to actions or processes of a machine (e.g., a computer with a processing element and other computer hardware components) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

Although the invention has been described with reference to the embodiments illustrated in the attached drawing figures, it is noted that equivalents may be employed and substitutions made herein without departing from the scope of the invention as recited in the claims.

We claim:

1. A system for evaluating an insurance applicant as part of an underwriting process to determine one or more terms of insurance coverage, the system comprising:
 a data receiving circuit configured to receive moving image and audio data of the insurance applicant; and
 a processor comprising an electronic circuit—
  trained to correlate aspects of appearance and voice with a personal and/or health-related characteristic by being provided with a database of moving image and audio data of individuals having known personal and/or health-related characteristics, and
  configured to analyze the moving image and audio data of the insurance applicant to determine the personal and/or health-related characteristic for the insurance applicant, and to suggest a term of insurance coverage based at least in part on the determined personal and/or health-related characteristic.

2. The system as set forth in claim 1, wherein the insurance coverage is life insurance coverage.

3. The system as set forth in claim 1, wherein the term of insurance coverage includes an insurance premium or discount.

4. The system as set forth in claim 1, wherein the moving image data of the insurance applicant includes a digital image.

5. The system as set forth in claim 1, wherein the moving image data of the insurance applicant includes an analog image.

6. The system as set forth in claim 1, wherein the processor is further—
 trained to correlate aspects of appearance with the personal and/or health-related characteristic by being provided with additional data of the database comprising still image data of individuals having the known personal and/or health-related characteristics,
 configured to determine the personal and/or health-related characteristic for the insurance applicant in part by analyzing a still image of the insurance applicant.

7. The system as set forth in claim 6, wherein the still image of the insurance applicant is an otherwise non-diagnostic conventional image.

8. The system as set forth in claim 7, wherein the still image of the insurance applicant is a selfie taken by the insurance applicant.

9. The system as set forth in claim 1, wherein the processor is trained using supervised machine learning.

10. The system as set forth in claim 1, wherein training the processor is trained using unsupervised machine learning.

11. The system as set forth in claim 1, wherein the processor employs a neural network.

12. The system as set forth in claim 11, wherein the neural network is a convolutional neural network.

13. The system as set forth in claim 11, wherein the neural network is a deep learning neural network.

14. The system as set forth in claim 1, wherein the personal and/or health-related characteristic is selected from the group consisting of: age, sex, weight, height, ethnicity, lifespan, cause of death, tobacco use, alcohol use, drug use, diet, and existing medical conditions, risk factors for future medical conditions.

15. The system as set forth in claim 1, wherein the processor is further configured to use the determined personal and/or health-related characteristic to verify information provided by the insurance applicant.

16. The system as set forth in claim 1, wherein the processor is further configured to use the determined personal and/or health-related characteristic to substantially automatically determine the term of coverage.

17. A system for evaluating an insurance applicant as part of an underwriting process to determine a life insurance premium, the system comprising:
- a data receiving circuit configured to receive otherwise non-diagnostic conventional moving image and audio data of the insurance applicant; and
- a processor comprising an electronic circuit employing a neural network and—
  - trained to correlate one or more aspects of appearance and/or voice with a personal and/or health-related characteristic by being provided with a database of otherwise non-diagnostic conventional moving image and audio data of individuals having known personal and/or health-related characteristics, and
  - configured to analyze the otherwise non-diagnostic conventional moving image and audio data of the insurance applicant to determine the personal and/or health-related characteristic for the insurance applicant, to use the determined personal and/or health-related characteristic to verify information provided by the insurance applicant, and to substantially automatically determine the life insurance premium based at least in part on the determined personal and/or health-related characteristic.

* * * * *